(12) United States Patent
Utani et al.

(10) Patent No.: US 11,564,849 B2
(45) Date of Patent: Jan. 31, 2023

(54) SYSTEM AND METHOD FOR FOLDING ARTICLE

(71) Applicant: ZUIKO CORPORATION, Osaka (JP)

(72) Inventors: Kouji Utani, Osaka (JP); Daisuke Inoue, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 968 days.

(21) Appl. No.: 16/340,359

(22) PCT Filed: Sep. 11, 2017

(86) PCT No.: PCT/JP2017/032659
§ 371 (c)(1),
(2) Date: Apr. 8, 2019

(87) PCT Pub. No.: WO2018/079100
PCT Pub. Date: May 3, 2018

(65) Prior Publication Data
US 2019/0240076 A1    Aug. 8, 2019

(30) Foreign Application Priority Data

Oct. 28, 2016 (JP) .............................. JP2016-211854

(51) Int. Cl.
*B65H 45/22* (2006.01)
*A61F 13/15* (2006.01)
(Continued)

(52) U.S. Cl.
CPC ........ *A61F 13/15747* (2013.01); *A61F 13/15* (2013.01); *A61F 13/476* (2013.01);
(Continued)

(58) Field of Classification Search
CPC ......... B41F 13/58; B65H 45/08; B65H 45/22; B65H 45/228; B41L 43/00; B41L 43/02
See application file for complete search history.

(56) References Cited

U.S. PATENT DOCUMENTS 802,057 A  * 10/1905 Nind et al.
5,807,228 A  *  9/1998 Smithe .................. B65H 45/22
                                              493/438
(Continued)

FOREIGN PATENT DOCUMENTS

JP          H9-567 A     1/1997
JP       H11-506965 A    6/1999
(Continued)

OTHER PUBLICATIONS

International Search Report Issued in PCT/JP2017/032659 dated Nov. 28, 2017 (with English translation).

*Primary Examiner* — Leslie A Nicholson, III
(74) *Attorney, Agent, or Firm* — Renner, Otto, Boisselle & Sklar, LLP

(57) ABSTRACT

A method in which, while an article is carried with a main portion in contact with a carrying surface and a to-be-folded portion in contact with a folder plate, includes: a first guiding step, wherein a first guide surface guides the to-be-folded portion of the unfolded article, on a side of the carrying surface, in parallel to the carrying surface; a second guiding step, following the first guiding step, wherein a second guide surface, while being in contact with the to-be-folded portion, gradually raises the to-be-folded portion while moving downstream; and a third guiding step, following the second guiding step, wherein a third guide surface guides the to-be-folded portion so that the to-be-folded portion is folded onto the main portion.

7 Claims, 6 Drawing Sheets

(51) Int. Cl.
*B65H 29/24* (2006.01)
*A61F 13/49* (2006.01)
*A61F 13/476* (2006.01)
*B65H 45/24* (2006.01)
*B65H 45/12* (2006.01)

(52) U.S. Cl.
CPC ........... *A61F 13/49* (2013.01); *B65H 29/242* (2013.01); *B65H 45/12* (2013.01); *B65H 45/22* (2013.01); *B65H 45/24* (2013.01)

(56) References Cited

U.S. PATENT DOCUMENTS

| | | | |
|---|---|---|---|
| 5,868,727 A | 2/1999 | Barr et al. | |
| 6,015,934 A * | 1/2000 | Lee | B65H 45/22 |
| | | | 604/387 |
| 6,210,309 B1 * | 4/2001 | Smithe | B65H 45/22 |
| | | | 493/438 |
| 6,699,166 B2 * | 3/2004 | Walter | B65H 45/22 |
| | | | 493/434 |
| 7,500,941 B2 * | 3/2009 | Coe | A61F 13/15747 |
| | | | 493/438 |
| 9,108,819 B2 * | 8/2015 | Murakami | B65H 45/08 |
| 2012/0207871 A1 | 8/2012 | Yamamoto | |
| 2013/0296152 A1 | 11/2013 | Murakami et al. | |

FOREIGN PATENT DOCUMENTS

| | | |
|---|---|---|
| JP | 2011-120745 A | 6/2011 |
| WO | WO 97-34556 A2 | 9/1997 |
| WO | WO 2011-025034 A1 | 3/2011 |
| WO | WO 2012-060249 A1 | 5/2012 |

\* cited by examiner

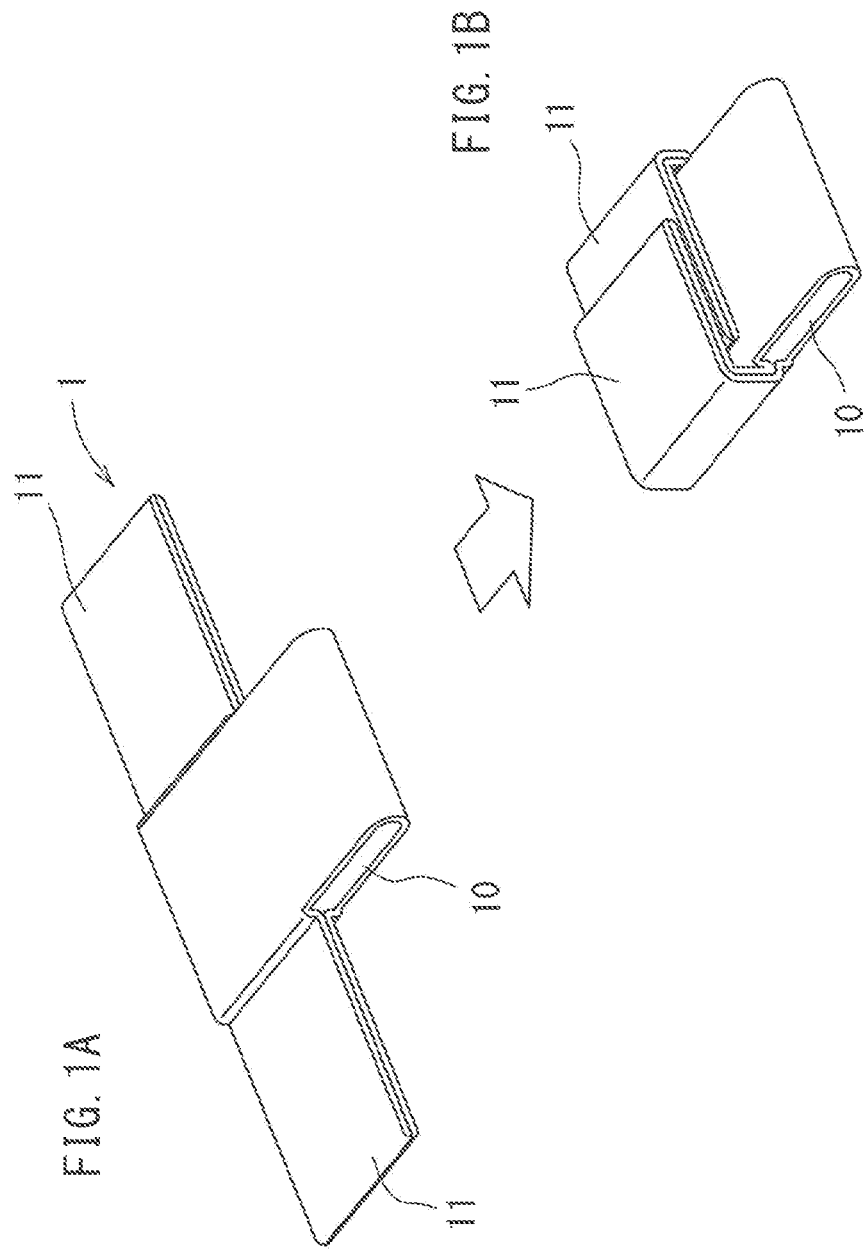

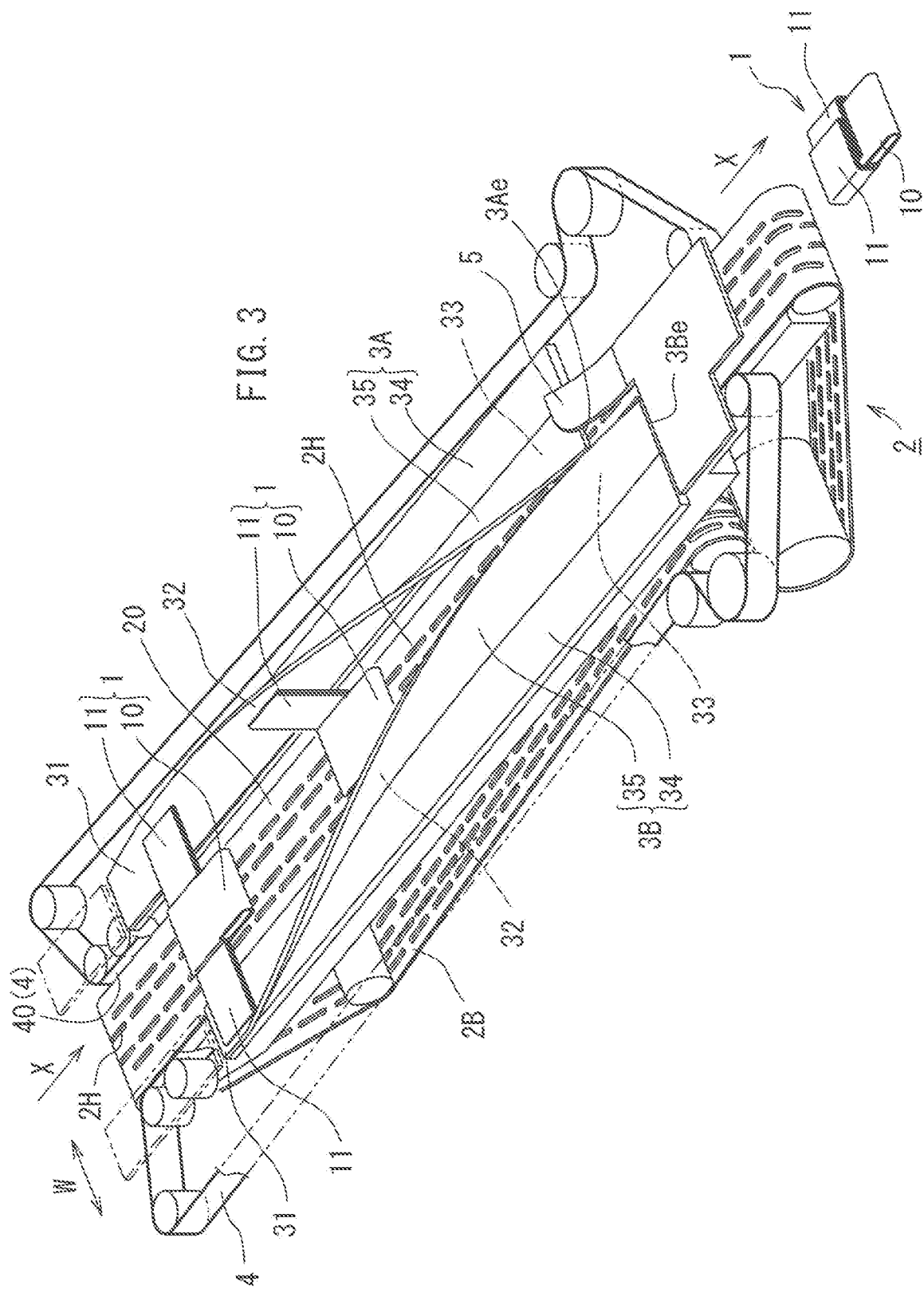

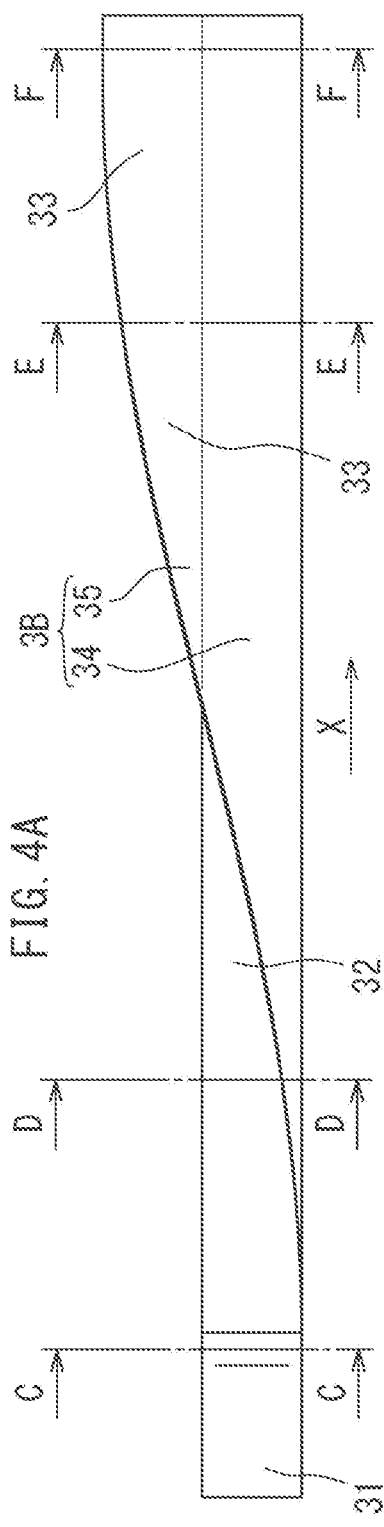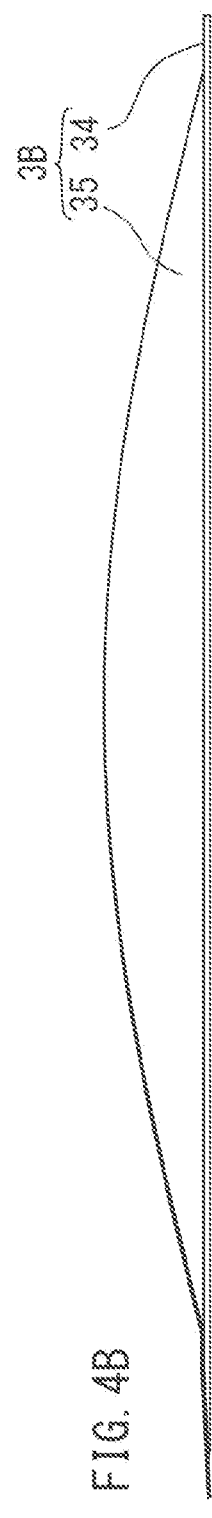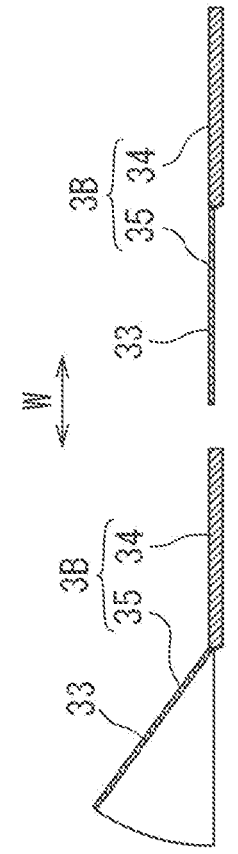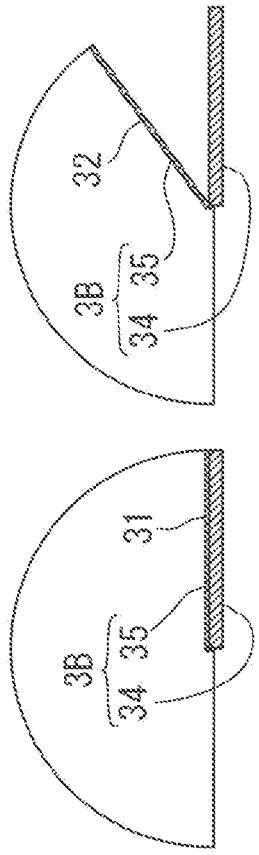

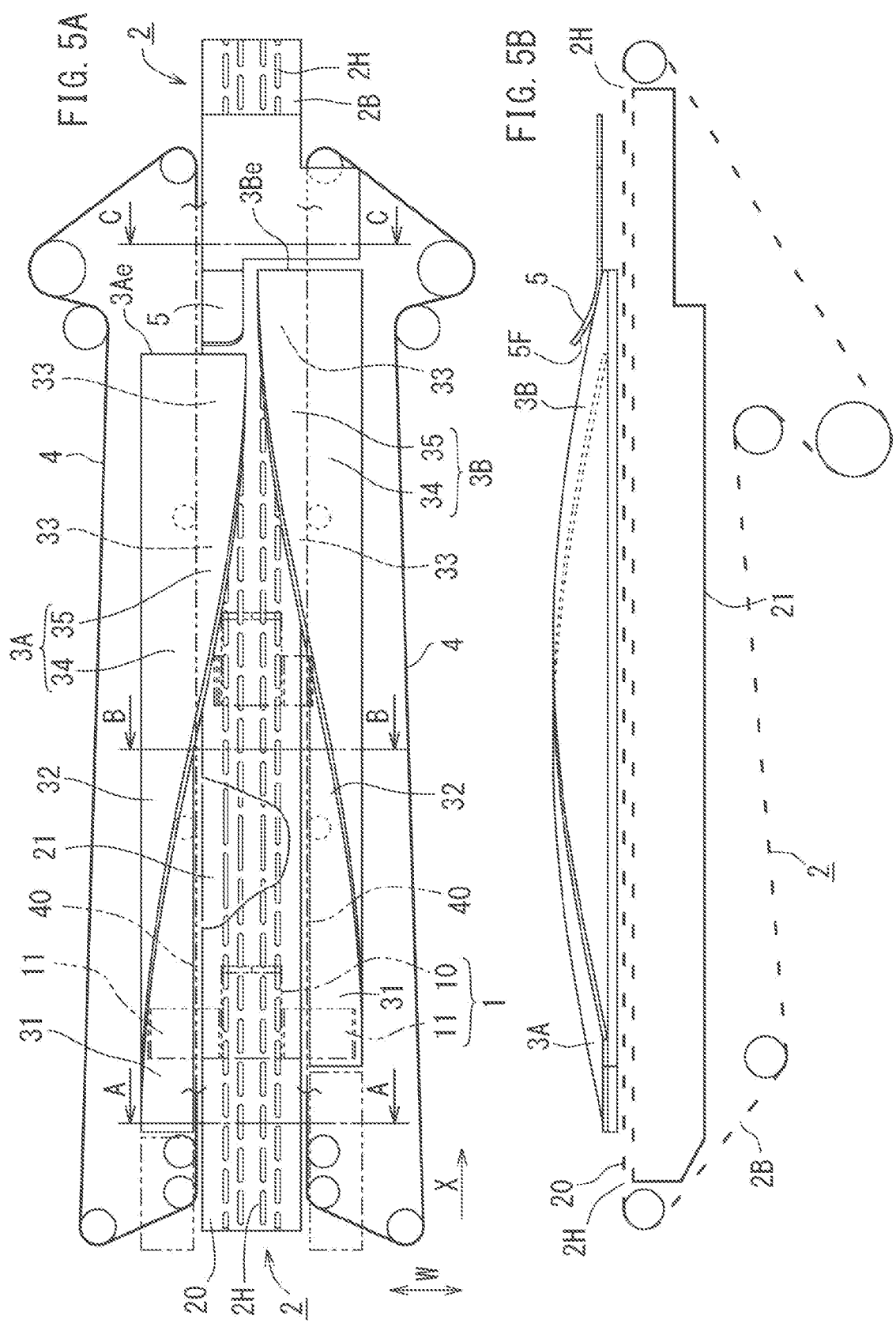

SYSTEM AND METHOD FOR FOLDING ARTICLE

TECHNICAL FIELD

The present invention relates to a system and a method for folding an article such as a worn article.

BACKGROUND ART

With the conventional technique identified below, folder plates are provided on the sides of the carrier section along which a continuous material is carried. The folder plates are provided in parallel to the carrying surface and include edge portions with. which to-be-folded portions come into contact for guiding the continuous material in the folding direction.

CITATION LIST

Patent Literature

[First Patent Document] WO2011/025034 (FIG. 1)

SUMMARY OF INVENTION

However, although the conventional technique discloses folding a continuous material, it does not disclose folding separated articles.

When one attempts to perform folding of a separated article such as a worn article, for example, by using the conventional technique, to-be-folded portions of the article are guided so as to come into contact with the edge portions of the folder plates. Therefore, it is likely that the to-be-folded portions flutter, failing to realize accurate folding.

It is an object of the present invention is to provide a folding system and a folding method with which it is possible to accurately fold to-be-folded portions of an article.

A folding system of the present invention is a folding system for folding an article 1 that has a main portion 10 and a to-be-folded portion 11 at least on one side of the main portion 10, the folding system including:

a carrier section 2 having a carrying surface 20 in contact with the main portion 10 for carrying the main portion. 10; and a folder plate 3A, 3B provided so as to correspond to the to-be-folded portion 11, the folder plate 3A, 3B including:

a first guide surface 31 provided in parallel to the carrying surface 20 on a side of the carrying surface 20 for guiding the to-be-folded portion 11 of the article 1 before the article 1 is folded;

a second guide surface 32 that gradually rises while extending downstream from the first guide surface 31 to raise the to-be-folded portion 11 while being in contact with the to-be-folded portion 11; and a third guide surface 33 that gradually turns to face the carrying surface 20 while extending downstream from the second guide surface 32 for guiding the to-be-folded portion 11 so that the to-be-folded portion 11 is folded onto the main portion 10.

A folding method of the present invention using such a folding system is carried out while the article 1 is carried with the main portion 10 in contact with the carrying surface 20 and the to-be-folded portion 11 in contact with the folder plate 3A, 3B, the folding method including:

a first guiding step, wherein the first guide surface 31 guides the to-be-folded portion 11 of the article 1 before the article 1 is folded, on a side of the carrying surface 20, in parallel to the carrying surface 20;

a second guiding step, following the first guiding step, wherein the second guide surface 32, while being in contact with the to-be-folded portion 11, gradually raises the to-be-folded portion 11 while moving downstream; and a third guiding step, following the second guiding step, wherein the third guide surface 33 guides the to-be-folded portion 11 so that the to-be-folded portion 11 is folded onto the main portion 10.

According to the present invention, the articles 1 are carried, one after another, with the main portion 10 of each article 1 on the carrying surface 20, wherein the to-be-folded portions 11 are folded so that the to-be-folded portions 11 are folded onto the main portion 10.

That is, the to-be-folded portions 11 are carried from the first guide surface 31 onto the second guide surface 32 so as to gradually rise while being carried downstream. Moreover, the to-be-folded portions 11 are guided from the second guide surface 32 to the third guide surface 33 so as to be folded so that the to-be-folded portions 11 are folded onto the main portion 10.

Thus, the to-be-folded portions 11 of the individual articles 1 are guided, one after another, along the first guide surface 31, the second guide surface 32 and the third guide surface 33, and the to-be-folded portions 11 will therefore be folded accurately without fluttering.

BRIEF DESCRIPTION OF DRAWINGS

FIG. 1A and FIG. 1B are perspective views showing an example of an article before and after the article is folded, respectively.

FIG. 3 is a perspective view showing one embodiment of a folding system of the present invention.

FIG. 4A and FIG. 4B are a plan view and a side view showing a second folder plate, and FIG. 4C, FIG. 4D, FIG. 4E and FIG. 4F are cross-sectional views of the folder plate.

FIG. 5A and FIG. 5B are a plan view and a partially-cross-sectional side view, respectively, of the folding system.

DESCRIPTION OF EMBODIMENTS

Figure 2A:
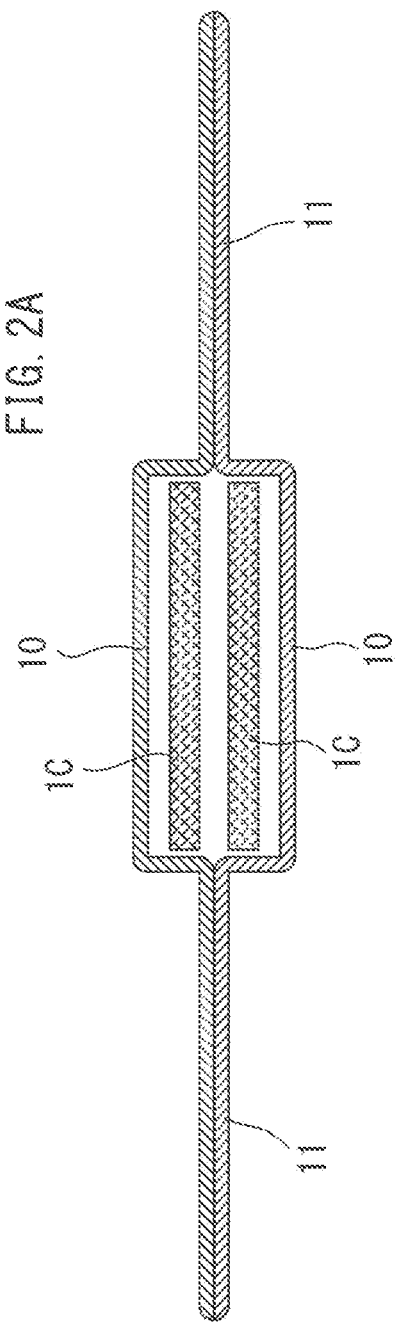
FIG. 2A and FIG. 2B are cross-sectional views showing the same.

Preferably, the first, second and third guide surfaces 31 to 33 are formed integrally (seamlessly) together, wherein the first guide surface 31 and the second guide surface 32 are formed continuously smoothly (seamlessly) together, and the second guide surface 32 and the third guide surface 33 are formed continuously smoothly (seamlessly) together.

In such a case, the to-be-folded portions 11 will be folded smoothly by being guided along the first to third guide surfaces.

In the present system, the main portion 10 of the article 1 may be an absorbent body including an absorbent core 1C, and the to-be-folded portion 11 of the article 1 may be a flap that is thinner than the main portion 10.

Preferably, the first guide surface 31 is arranged at a level above the carrying surface 20;

a pair of fourth guide surfaces 40 are arranged below the first guide surface 31 on both sides of the carrying surface 20 for guiding opposite sides of the main portion 10, which is thicker than the flap; and the fourth guide surfaces 40 are each arranged along a virtual plane that crosses the first guide surface 31.

In such a case, the fourth guide surfaces 40 guide the side surfaces of the main portion 10, thereby preventing the article 1 from assuming an inadvertent attitude on the carrying surface 20.

Preferably, the carrying surface 20 is composed of a surface of a belt 2B that rotates, and the carrying surface 20 has a plurality of suction holes 2H formed therein for sucking the main portion 10 via a vacuum.

Thus, by providing a plurality of suction holes 2H in the belt 2B so as to carry the main portion 10 while sucking the main portion 10 via a vacuum, and. further folding, the attitude of the main portion 10 will be prevented from being disturbed.

Preferably, the folder plate 3A, 3B includes a first folder plate 3A provided on one side of the carrying surface 20 and a second folder plate 3B provided on the other side of the carrying surface 20; and the plates are arranged with a phase difference from each other in a flow direction of the article 1 so that a terminal 3Ae of the first folder plate 3A is located upstream, in the flow direction, of a terminal 3Be of the second folder plate 3B.

In such a case, the pair of to-be-folded portions 11 can be folded.

Regarding their terminal positions, the first folder plate 3A is arranged upstream and the second folder plate 3B is arranged downstream. Therefore, it is possible to fold one to-be-folded portion 11 onto the main portion 10 and then fold the other to-be-folded portion 11 onto the main portion 10. p More preferably, the folding system further includes a hold plate 5 provided downstream of the terminal of the first folder plate 3A for holding down the article 1 whose to-be-folded portion 11 is folded onto the main portion 10, wherein the hold plate 5 includes a slope 5F that is spaced apart above the carrying surface 20 at an upstream end of the hold plate 5 in the flow direction, and that extends diagonally downward while extending downstream for holding down the article.

In such a case, one of the to-be-folded portions 11 that has been first folded by the first folder plate 3A is held down by the hold plate 5, and it is therefore possible to maintain the folded state of the to-be-folded portion 11 that has been folded.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

Embodiments

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

One embodiment of the present invention will now be described with reference to the drawings.

The description of the present embodiment will be directed to disposable worn articles such as disposable pants and diapers, for example, as shown in FIG. 1A and FIG. 1B.

In FIG. 1A, an article 1 includes a main portion 10, and to-be-folded portions 11 protruding on the opposite sides of the main portion 10. As shown in FIG. 2A, the main portion 10 of the article 1 is an absorbent body that includes an absorbent core 1C. The to-be-folded portions 11 of the article 1 are flaps that are thinner than the main portion 10.

Figure 2B:
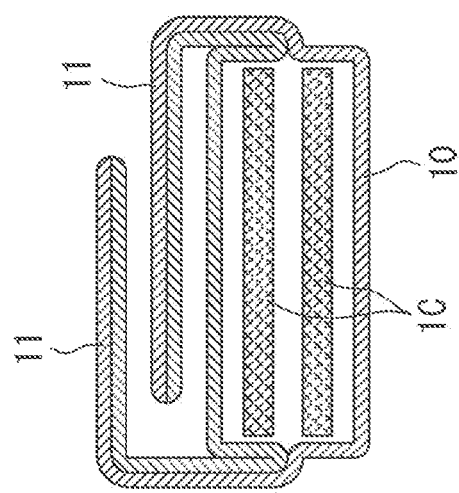

As shown in FIG. 2B, the article 1 is folded by a folding system so that the pair of flaps 11 are folded onto the absorbent body.

As shown in FIG. 3, the present system includes a carrier section 2, a pair of folder plates 3A and 3B, a pair of guide belts 4, a hold plate 5, etc. The carrier section 2 has a carrying surface 20 to be in contact with the main portion 10, and carries the main portion 10. The folder plates 3A and 3B are provided corresponding to the to-be-folded portions 11, and fold the to-be-folded portions 11 onto the main portion 10.

In FIG. 3, the carrying surface 20 is composed of a belt 2B that rotates. The carrying surface 20 has many suction holes 211 formed therein for sucking the main portion 10 via a vacuum.

The belt 2B is rotated by a motor (not shown). As clearly shown in FIG. 6A to FIG. 6C and FIG. 5B, the belt 2B forms a well-known belt conveyer, and is provided endlessly along a vacuum box 21.

As shown in FIG. 3 and FIG. 5A, the first and second folder plates 3A and 3B are provided on the opposite sides of the carrying surface 20 in the width direction W. The first and second folder plates 3A and 3B have a phase difference from each other in the flow direction X of the article 1.

That is, the plates 3A and 3B are arranged with a phase difference from each other in the flow direction of the article 1 so that a terminal 3Ae of the first folder plate 3A of FIG. 3 is located upstream, in the flow direction, of a terminal 3Be of the second folder plate 3B.

The plates 3A and 3B are arranged in symmetry with. each other with respect to the belt 2B, and have substantially the same structure. The following description will primarily focus on the second folder plate 3B, of the two plates.

The second folder plate 3B includes first, second and third guide surfaces 31 to 33, which are formed integrally together, wherein the guide surfaces 31 to 33 are formed continuously smoothly together. The guide surfaces 31 to 33 are arranged at a level above the carrying surface 20. Therefore, edges of the to-be-folded portions 11 are guided while being in contact with the guide surfaces 31 to 33.

In FIG. 3, the first guide surface 31 is provided beside the carrying surface 20 in parallel to the carrying surface 20 for guiding the to-be-folded portions 11 of the unfolded (not-yet folded) article 1.

The second guide surface 32 gradually rises while extending downstream from the first guide surface 31 to raise the to-be-folded portions 11 while being in contact with the to-be-folded portions 11.

The third guide surface 33 gradually turns to face the carrying surface 20 while extending downstream from the second guide surface 32 for guiding the to-be-folded portions 11 so that the to-be-folded portions 11 are folded onto the main portion 10.

FIG. 4A to FIG. 4F show details of the second folder plate 3B and the first to third guide surfaces 31 to 33.

As shown in FIG. 4C to FIG. 4F, the second folder plate 3B includes a base plate 34, and a twisted plate 35 welded to the base plate 34. As shown in FIG. 4A to FIG. 4F, the twisted plate 35 is twisted gradually to form the first to third guide surfaces 31 to 33.

Note that the base plate 34 may be formed with a plurality of long holes that allow the second folder plate 3B to be secured to the frame of the carrier section 2 so that the position thereof can be adjusted.

FIG. 4C shows the first guide surface 31. As can be seen from FIG. 4A, FIG. 4B and FIG. 6A, the first guide surface 31 is parallel to the carrying surface 20 of the belt 2B, and is set at a level that is slightly higher than the carrying surface 20 so as to be located above the carrying surface 20 of FIG. 6A.

Figure 6A:
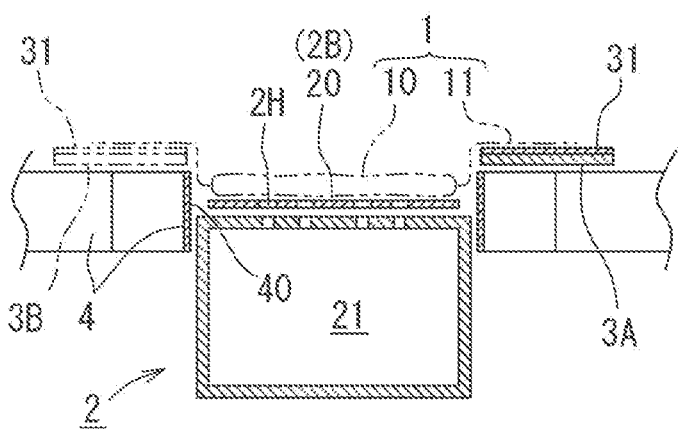
FIGS. 6A to 6C are transverse cross-sectional views of FIG. 5A showing a folding method.

Note that in FIG. 6A, the difference in level in the vertical direction between the first guide surface 31 and the carrying surface 20 is exaggerated for the sake of illustration.

Figure 6B:
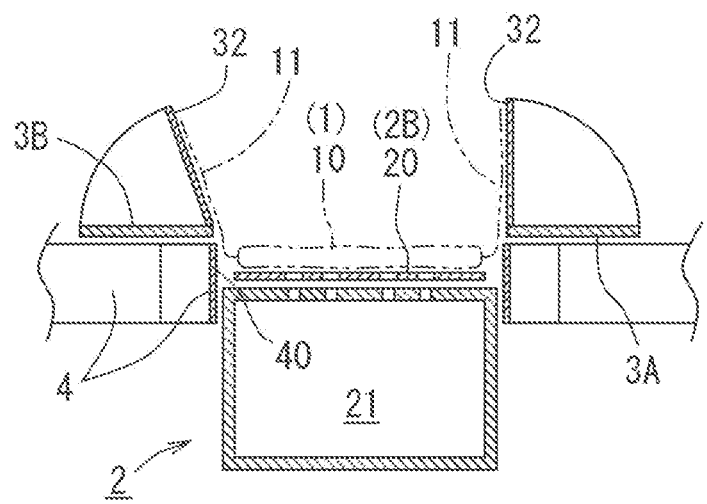

FIG. 4D shows the second guide surface 32. As can be seen from. FIG. 4D, FIG. 4E and FIG. 4A, the second guide surface 32 is twisted spirally. As shown in FIG. 4D and FIG. 6B, the second guide surface 32 gradually raises the to-be-folded portions 11.

FIG. 4E and FIG. 4F show the third guide surface 33. As can be seen from FIG. 4D, FIG. 4E, FIG. 4A and FIG. 3, the upstream portion of the third guide surface 33 is smoothly continuous with the second guide surface 32 and twisted spirally to face the carrying surface 20 of the belt 2B. The downstream portion of the third guide surface 33 shown in. FIG. 4F and FIG. 4B faces and is parallel to the carrying surface 20 of the belt 2B of FIG. 6C. The third guide surface 33 guides the to-be-folded portions 11 so that the to-be-folded portions 11 of FIG. 3 are folded onto the main portion 10.

Figure 6C:
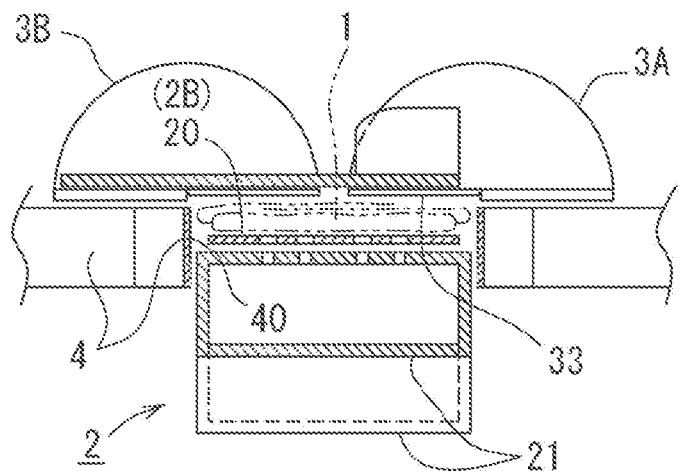

The phase of the first to third guide surfaces 31 to 33 of FIG. 6A to FIG. 6C is such that the first folder plate 3A is arranged more upstream than the second folder plate 3B, as can be seen from FIG. 5A and FIG. 3.

The hold plate 5 extends, downstream of the terminal 3Ae of the first folder plate 3A, while being bent upward over the first folder plate 3A, and holds down the article 1 whose to-be-folded portions 11 are folded onto the main portion 10. The hold plate 5 is spaced apart above the carrying surface 20 at the upstream end in the flow direction, and includes a slope 5F that extends diagonally downward while extending downstream for holding down the article.

In FIG. 3, the guide belts 4 are arranged on the opposite sides of the carrier section 2 Each guide belt 4 is rotated and forms a fourth guide surface 40.

On both sides of the carrying surface 20, the guide belts 4 of FIG. 6A to FIG. 6C guide the opposite sides of the main portion 10, which is thicker than the flaps. That is, the fourth guide surface 40 is arranged below the first guide surface 31, and is arranged along a plane that is perpendicular to the first guide surface 31.

Next, a folding method will be described. As shown in FIG. 3, the folding method using the present folding system is carried out as described below while the article 1 is carried by the belt 2B, with the main portion 10 in contact with the carrying surface 20 and the to-be-folded portions 11 in contact with the folder plates 3A and 3B.

The unfolded (not-yet folded) article 1 of FIG. 3 is introduced into the carrier section 2 from upstream.

The unfolded article 1 is carried downstream X while the main portion 10 thereof is held by suction on the belt 2B, and the to-be-folded portions 11 of the article 1 are carried so as to slide on the first guide surface 31. In the first guiding step, as shown in FIG. 6A, the first guide surface 31 guides the to-be-folded portions 11 of the unfolded article 1, on the sides of the carrying surface 20, in parallel to the carrying surface 20.

In FIG. 3, the second guiding step is performed, following the first guiding step. That is, the spiral-shaped second guide surface 32, while being in contact with the to-be-folded portions 11, gradually raises the to-be-folded portion 11 while moving downstream, as shown in FIG. 6B.

In FIG. 3, the third guiding step is performed, following the second guiding step. That is, the spiral-shaped portion of the third guide surface 33, which is continuous with the second guide surface 32, while being in contact with the to-be-folded portions 11, gradually folds the to-be-folded portions 11 while moving downstream. The third guide surface 33 of FIG. 6C is twisted until it faces parallel to the second guide surface 32, and in the third guiding step, the to-be-folded portions 11 are guided by the third guide surface 33 so that the to-be-folded portions 11 of FIG. 3 are folded onto the main portion 10.

The series of folding actions occur on both of the first and second folder plates 3A and 3B of FIG. 3. Herein, the phase of the second folder plate 3B is shifted downstream in the flow direction X with respect to that of the first folder plate 3A. Thus, the pair of to-be-folded portions 11 are folded with slightly different timings, as shown in FIG. 3 and FIG. 6B. Therefore, it is possible, with the pair of folder plates 3A and 3B, to fold the pair of to-be-folded portions 11 onto each other.

INDUSTRIAL APPLICABILITY

The present invention is applicable to folding various articles such as worn articles.

REFERENCE SIGNS LIST

1: Article, 10: Main portion, 11: To-be-folded portions
1C: Absorbent core
2: Carrier section, 20: Carrying surface, 2B: Belt, 2H: Suction hole, 21: Vacuum box
3A: First folder plate, 3B: Second folder plate, 3Ae, 3Be: Terminal
31: First guide surface, 32: Second guide surface, 33: Third guide surface
34: Base plate, 35: Twisted plate
4: Guide belt, 40: Fourth guide surface
5: Hold plate, 5F: Slope
X: How direction, W: Width direction

The invention claimed is:

1. A folding system for folding an article that has a main portion and a to-be-folded portion at least on one side of the main portion, the folding system comprising:
　a carrier section having a carrying surface in contact with the main portion for carrying the main portion; and
　a first folder plate provided on one side of the carrying surface and a second folder plate provided on another side of the carrying surface, the first and second folder plates provided so as to correspond to the to-be-folded portion, each of the first and second folder plate comprising:
　　a first guide surface provided in parallel to the carrying surface on a side of the carrying surface for guiding the to-be-folded portion of the article before the article is folded;
　　a second guide surface that gradually rises while extending downstream from the first guide surface to raise the to-be-folded portion while being in contact with the to-be-folded portion; and a third guide surface that gradually turns to face the carrying surface while extending downstream from the second guide surface for guiding the to-be-folded portion so that the to-be-folded portion is folded onto the main portion, wherein the first and the second folder plates are arranged with a phase difference from each other in a flow direction of the article so that a terminal of the first folder plate is located upstream, in the flow direction, of a terminal of the second folder plate and the first guide surface of the second folder plate is located upstream, in the flow direction, of the terminal of the first folder plate.

2. The folding system according to claim 1, wherein the first, second and third guide surfaces are formed integrally together, wherein the first guide surface and the second guide surface are formed continuously smoothly together, and the second guide surface and the third guide surface are formed continuously smoothly together.

3. The folding system according to claim 1, wherein the main portion of the article is an absorbent body including an absorbent core, and the to-be-folded portion of the article is a flap that is thinner than the main portion.

4. The folding system according to claim 3, wherein:
the first guide surface is arranged at a level above the carrying surface;
a pair of fourth guide surfaces are arranged below the first guide surface on both sides of the carrying surface for guiding opposite sides of the main portion, the main portion being thicker than the flap; and
the fourth guide surfaces are each arranged along a plane that crosses the first guide surface.

5. The folding system according to claim 1, wherein the carrying surface is composed of a surface of a belt that rotates, and the carrying surface has a plurality of suction holes formed in the carrying surface for sucking the main portion via a vacuum.

6. The folding system according to claim 1, further comprising a hold plate provided downstream of the terminal of the first folder plate for holding down the article whose to-be-folded portion is folded onto the main portion, wherein the hold plate includes a slope, the slope being spaced apart above the carrying surface at an upstream end of the hold plate in the flow direction and extending diagonally downward while extending downstream for holding down the article, and at least a part of the hold plate is located upstream in the flow direction, of the terminal of the second folder plate.

7. A folding method using folding system according to claim 1, wherein:

the folding method is carried out while the article is carried with the main portion in contact with the carrying surface and the to-be-folded portion in contact with the folder plate, the folding method comprising:

a first guiding step, wherein the first guide surface guides the to-be-folded portion of the article before the article is folded, on a side of the carrying surface, in parallel to the carrying surface;

a second guiding step, following the first guiding step, wherein the second guide surface, while being in contact with the to-be-folded portion, gradually raises the to-be-folded portion while the to-be-folded portion is moving downstream; and a third guiding step, following the second guiding step, wherein the third guide surface guides the to-be-folded portion so that the to-be-folded portion is folded onto the main portion.

* * * * *